United States Patent [19]

Meares et al.

[11] Patent Number: 4,622,420

[45] Date of Patent: Nov. 11, 1986

[54] CHELATING AGENTS AND METHOD

[75] Inventors: Claude F. Meares; Simon M. Yeh; David G. Sherman, all of Davis, Calif.

[73] Assignee: The Regents of the University of California, Berkeley, Calif.

[21] Appl. No.: 698,354

[22] Filed: Feb. 5, 1985

Related U.S. Application Data

[63] Continuation of Ser. No. 389,755, Jun. 18, 1982, abandoned, which is a continuation of Ser. No. 131,684, Mar. 18, 1980, abandoned.

[51] Int. Cl.$^4$ ............................................. C07C 101/26
[52] U.S. Cl. ..................... 562/443; 562/565; 562/556; 562/564; 562/448; 548/496; 548/450; 534/573; 534/558
[58] Field of Search ............................ 260/429 J, 141; 562/438, 450, 442, 443, 444, 565, 448, 556, 564; 548/496; 534/558, 573

[56] References Cited

U.S. PATENT DOCUMENTS

| | | | |
|---|---|---|---|
| 2,893,916 | 7/1959 | Rubin | 260/429 J |
| 3,062,719 | 11/1962 | Rubin et al. | 562/565 |
| 3,780,100 | 12/1973 | Scanlon et al. | 260/429 J |
| 3,994,966 | 11/1976 | Sundberg et al. | 562/443 |
| 4,043,998 | 8/1977 | Meares et al. | 562/443 |
| 4,352,751 | 10/1982 | Wieder et al. | 562/565 |
| 4,432,907 | 2/1984 | Wieder et al. | 260/429 J |

FOREIGN PATENT DOCUMENTS 828547 1/1952 Fed. Rep. of Germany ...... 562/565

OTHER PUBLICATIONS

*Journal of Radioanalytical Chemistry*, vol. 53, No. 1–2 (1979) pp. 327–336.
Analytical Biochemistry 100, pp. 152–159 (1979).
JACS, 92:6 (1970), pp. 1637–1646.
*Chemistry of Amino Acids*, Greenstein, pp. 927–933.
Tetahedron, vol. 24, pp. 1145–1162 (1968).
JACS, vol. 81, pp. 2955–2957 (1959).
Chem. Pharm. Bull., vol. 13 (1), pp. 88–93 (1965).
J. Med. Chem., 17, 1304–1307 (1974).
Proc. Nat'l. Acad. Sci., U.S.A., 73, pp. 3803, 3806 (1976).
ACS/CSJ Chemical Congress, Abstracts of Papers, Apr. 1–6, 1979, No. 53.
J. Med. Chem., vol. 19, pp. 962–964 (1976).
J. Pharm. Sci., vol. 64, pp. 704–706 (1975).
Biochem. & Biophys. Res. Com., vol. 22, pp. 581–585 (1977).
Bull. Chem. Soc. Japan, vol. 40, pp. 2326–2332 (1967).
J. Org. Chem., vol. 36, No. 17, pp. 2548–2550 (1971).
Bull. Chem. Soc. Japan, 45, M. Saburi et al., pp. 806–811, 1086–1093 (1972).
*Chelating Agents and Metal Chelates*, (ed. Dwyer et al.), Academic Press (1964), pp. 283–289, 328–331.
J. Org. Chem., vol. 41, No. 7, Roeske, et al., pp. 1260–1261 (1976).

Primary Examiner—James H. Reamer
Attorney, Agent, or Firm—Ciotti & Murashige

[57] ABSTRACT

A simple method for making EDTA, ED3A or DTPA analogs from amide derivatives of alpha amino acids is disclosed. These EDTA, ED3A or DTPA analogs are useful chelating agents, and preferably are useful as bifunctional chelating agents which may be attached to biological molecules and which form physiologically stable chelates with a variety of metal ions.

4 Claims, No Drawings

CHELATING AGENTS AND METHOD

This is a continuation of application Ser. No. 389,755, filed June 18, 1982 (now abandoned), which is a continuation of Ser. No. 131,684, filed Mar. 18, 1980 (now abandoned).

TECHNICAL FIELD

This invention relates generally to chelating agents, and more particularly to EDTA, ED3A and DTPA analogs formed from amino acid precursors which may be attached to biological molecules and which form physiologically stable chelates with a variety of metal ions.

The invention described herein was made in the course of, or under, a grant from the National Institutes of Health.

BACKGROUND ART

It is known that metal ions may be attached to biological molecules by means of bifunctional chelating agents. Such chelating agents are compounds which incorporate a covalent bond-forming moiety, which may be attached to a biological molecule, and a metal-binding moiety which forms a chelate with metal ions.

In 1974 M. W. Sundberg, et al, demonstrated a seven-step synthesis yielding a bifunctional chelating agent, p-nitrophenyl EDTA. *J. Med. Chem.*, 17, 1304 (1974). Several years later, using the seven-step synthesis of Sundberg, et al, such a para-substituted, 1-phenyl-EDTA compound was prepared, and chelates thereof were formed with $^{111}$indium. The radiolabelled chelates were demonstrated to be stable in vivo and in vitro. C. Meares, et al, *Proc. Natl. Acad. Sci. U.S.A.*, 73, 3803 (1976). Such radiolabelled chelates may be attached to the protein human serum albumin so that the product retains biological activity, and can thus serve as a in vivo radiotracer useful in clinical or diagnostic medicine. These para-substituted, 1-phenyl EDTA compounds known to the art, although forming a variety of stable chelates, have had the disadvantage in that their synthesis has been relatively difficult.

Various other chelating agents have also been used for in vivo radiotracer studies, but have been less stable than the 1-phenyl EDTA compounds; thus, a large portion of the radioactive metal ions has tended to be lost to the serum protein transferrin. This leads to deposition of radioactive metal ions in the liver and bone marrow.

Additionally, the prior known chelating agents have normally been optically inactive: either because they do not contain an asymmetric carbon atom, or because the syntheses yield a racemic mixture. It is believed that use of non-optically active chelating agents (or racemic mixtures) with biological molecules may tend to adversely affect the in vivo properties thereof.

The present invention is directed to overcoming one or more of the problems as set forth above.

DISCLOSURE OF THE INVENTION

In one aspect of the present invention, a method of making an optically active chelating agent comprises: providing an amide derivative of an optically active, alpha amino acid; reducing the amide derivative with borane; and, reacting the reduced amide derivative with a carboxy methylating agent. The alpha-amino acids from which the amides are derived are preferably the readily available, optically active and naturally occurring amino acids. The inventive method provides a simple route to a variety of chelating agents.

In another aspect of the present invention, a chelating agent comprises various particular EDTA, ED3A and DTPA analogs which readily form stable chelates with a variety of metal ions.

DETAILED DESCRIPTION OF THE PREFERRED EMBODIMENTS

The chelating agents of the present invention are derived from amides of optically pure and active alpha amino acids. The reactions leading to making the chelating agents of the present invention are stereospecific. Accordingly, the alpha amino acid amide precursors of the inventive chelating agents may belong to either the L or D stereochemical series, as follows.

All of the amino acids that have been found to naturally occur in proteins, except glycine, contain at least one asymmetric carbon atom, and are optically active. By convention, all naturally occurring amino acids found in proteins belong to the L stereochemical series, and are stereochemically related to L-glyceraldehyde. As is well known, but defined herein for purposes of clarity, these naturally occurring amino acids may be generally represented as is herein illustrated by Figure 1(a), below.

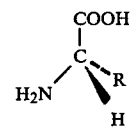

FIG. 1(a)

The enantiomer of Figure 1(a) is represented by Figure 1(b), below.

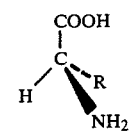

FIG. 1(b)

As illustrated by Figures 1(a) and 1(b), all of these alpha amino acids have a carboxyl group and an amino group at the carbon atom alpha to the carboxyl group. The R moiety, well known to the art, represents the variations among these amino acids. For example, the R moiety of tyrosine is $-CH_2-O-OH$; whereas, the R moiety for phenylalanine is $-Ch_2-O$. Substantially all of the optically pure and active alpha amino acids, when of either the L or D configuration, are useful as precursors for preparing the inventive chelating agents. Among preferred precursor amino acids are: tyrosine, phenylalanine, alanine, tryptophan, cysteine, and lysine. Additionally, certain modified alpha amino acids are useful as precursors for preparing the inventive chelating agents. Among preferred precursor modified alpha amino acids are optically pure and active methyl tyrosine, methyl tryptophan and p-nitro phenylalanine.

In the best mode contemplated for carrying out the present invention, the most preferred precursor amino acids are tyrosine and phenylalanine of the L stereochemical configuration. This is because the aromatic rings thereof assist in enhancing certain end uses for the inventive chelating agents, and because of the ready availability and purity of the naturally occuring alpha amino acids.

It is also believed that cysteine may provide particularly useful advantages for coupling with biological molecules. The end uses and advantages shall be further discussed after the following detailed description of the formation of the inventive chelating agents.

Method

A method of making an optically active chelating agent comprises providing an amide derivative of an optically active amino acid. Such an amide derivative is generally represented by either of the structures of Figure 2 below:

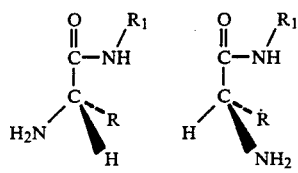

FIG. 2

The R moiety of Figure 2 is identical to, that is stems from, the R moiety of the particular amino acid precursor. The $R_1$ moiety includes a variety of species, depending upon the particular amine utilized in forming the amide derivative. For example, if the amine is ammonia, then $R_1=H$; if the amine is ethanolamine, then $R_1=CH_2CH_2OH$; if the amine is ethylenediamine, then $R_1=CH_2CH_2NH_2$.

The amide derivative has a carbonyl group. A carbon atom is alpha to the carbonyl group and has the original amino group of the alpha-amino acid bound thereto. These amide derivatives may be prepared by conventional peptide synthesis techniques or may in many instances be purchased from commercial sources. In any event, the alpha carbon continues to define the same optical configuration (the L or D stereochemical configuration) for the amide derivative as it did for the alpha amino acid precursor.

The carbonyl group of the amide derivative is then chemically reduced with borane to produce a diamine compound. Such a diamine compound is generally illustrated by Figure 3, below:

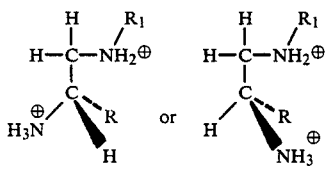

FIG. 3

The diamine compound thus has a pair of amine moieties with the alpha carbon therebetween. It has been found that the alpha carbon continues to define the same optical configuration for the diamine compound as it did for the amide. That is, the reduction of the amide derivative with borane preserves the original optical configuration. The $R_1$ moiety of Figure 3 is substantially identical to the $R_1$ moiety of Figure 2, with an exception being that the nitrogen atoms thereof will normally be protonated, each with a $H^+$ ion.

This diamine compound is then reacted with one of various conventional carboxymethylating agents. A chelating agent in accordance with the present invention is recovered therefrom, which has a general structure as represented by FIG. 4, below:

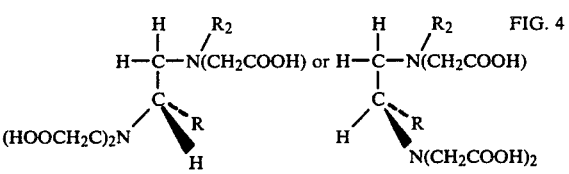

FIG. 4

The R moiety of the inventive chelating agent, as illustrated by Figure 4 above, is determined by the alpha amino acid precursor. As shall be later described, the R moiety may be subsequently modified if desired, so as to provide covalent bonding opportunities for use of the chelating agent as a bifunctional chelating agent. However, the reaction of the diamine compound with the carboxymethylating compound yields chelating agents having, that is continuing, the L or D sterochemical configuration.

The $R_2$ moiety is the same as, or is the carboxymethylated species from, the $R_1$ moiety of Figures 2 and 3. Thus, for example, where $R_1=H$, then $R_2=CH_2COOH$ and the chelating agent is an EDTA analog [wherein EDTA stands for ethylenediamine tetraacetic acid]. Where $R_1=CH_2CH_2OH$, then $R_2=CH_2CH_2OH$, and the chelating agent is a hydroxyethyl-ED3A analog [wherein ED3A stands for ethylenediamine triacetic acid]. Where $R_1=CH_2CH_2NH_2$, then $R_2=CH_2CH_2N(CH_2COOH)_2$, and the chelating agent is a DTPA analog [wherein DTPA stands for diethylenetriamine pentaacetic acid].

The inventive chelating agents and method shall now be more fully described. The experimental procedures and reagents were as follows.

NMR spectra were recorded at 60 MHz, on a Varian EM360 Spectrometer with t-butanol ($\delta=1.1$) as internal standard; pH meter readings were not corrected for the deuterium isotope effect. Fluorescence spectra were recorded on a Perkin-Elmer/Hitachi MPF2A fluorescence spectrophotometer, uncorrected for instrumental response. Optical rotation measurements were made at 23° using a 1 dm tube in a JEOL DIP-180 polarimeter. All TLC analyses were run in either solvent 1: n-amyl alcohol/pyridine/water (43/37/20), V/V), solvent 2: 95% ethanol/25% NH₄OH (4/1. V/V), solvent 3: 10% aq NH₄OAc/methanol (1/1, V/V), or solvent 4: 15 ml of 0.033 M HCl/35 ml of acetone, on silica gel F-254 plates (Merck) with fluorescent indicator. High voltage paper electrophoresis was run on Whatman 3 MM paper with a Savant HV 5000 UL 115-3 power supply, FP22A cooling plate, and RWC-50 UL recirculating water cooler. Radioactive samples were counted on a Beckman Gamma 310 instrument.

Carrier-free $^{111}InCl_3$ was obtained from Medi-Physics, Emeryville, Calif. and purified. $^{59}FeCl_3$ was obtained from New England Nuclear. Human serum albumin was purchased from Cutter Laboratories as a 25% solution. 1-ethyl-3-(3-dimethylaminopropyl)-carbodiimide was obtained from Calbiochem. Borane-tetrahydrofuran complex, L-phenylalanine, L-tryptophan, L-tyrosine, and bromoacetic acid were purchased from Aldrich. L-alanine, L-tyrosinamide, L-phenylalaninamide, and L-methyl tyrosine were purchased from Sigma. Dowex 50 and AG1 ion exchange resins and Biogel P-100 resin were Bio-Rad Laboratories, Inc. All other solvents and reagents used were the purest commercially available products.

Providing Step

The amide derivative of the alpha amino acid or alpha amino acid analog may be provided by converting the alpha amino acid or analog to an ester form, and then converting this ester form to an amide form. Procedures 1 and 2, as follows, illustrate these preferred ester forms and then the amide conversions for the providing step.

Procedure 1 amino acid→amino acid methyl ester

The amino acid can be converted to the ester in one of two ways. The amino acid is treated with Dowex 50W resin (H+) dried, 5.2 meq/g, in equimolar amounts in methanol. This two phase system is allowed to stir for 1-2 days. Alternatively, the amino acid can be treated with methanol saturated with HCl(g), in approximately 20 ml of methanol solution to 1 g of solid amino acid, and allowed to sit for 1-2 days. The course of the reaction can be followed by IR scan of the reaction solution, a change in carbonyl from about 1650 $cm^{-1}$ to about 1750 $cm^{-1}$ is expected, and the reaction is complete when the acid carbonyl is gone. (For the resin reaction, a sample of the resin should be treated with HCl(g) to liberate the amino acid ester into solution). The resin solution will be used as it is. The methanol/HCl solution is reduced to a solid under reduced pressure, solids recrystalized from ethanol. TLC were run in solvent 2.

Esters of the following compounds have been made:

| Amino Acid | A.A.Rf | Methanol | Ester Rf | Yield |
|---|---|---|---|---|
| Tyrosine | 0.56 | Both | 0.76 | 90% |
| Alanine | 0.57 | Resin | 0.76 | Undetermined |
| Phenylalanine | 0.58 | MeOH/HCl | 0.77 | 95% |
| Tryptophan | 0.58 | MeOH/HCl | 0.75 | 90% |
| 1-Methyl tryptophan | 0.55 | MeOH/HCl | 0.79 | 75% |
| $NO_2$ phenyl alanine | 0.58 | MeOH/HCl | 0.77 | 97% |
| Methyl tyrosine | 0.52 | MeOH/HCl | 0.80 | 95% |

Procedure 2

(amino acid methyl ester→amino acid amide)

The amino acid methyl ester can be converted to the primary amide by treating either the resin bound ester with repeated $NH_3(g)$ saturated methanol and filtering, or the amino acid methyl ester hydrochloride with $NH_3(g)$ saturated methanol, and leaving the methanol solution to sit for 3-7 days. The course of the reaction can be followed by monitoring the carbonyl peak on IR, as it changes from about 1750 $cm^{-1}$ to about 1620 $cm^{-1}$. Reaction is complete when the ester carbonyl is gone. The solvent is removed under reduced pressure, and TLC in solvent 2 shows one spot.

The primary amide derivatives of the following amino acid esters were made:

| Amino Acid Ester | Amide RF | Yield |
|---|---|---|
| Tyrosine | .63 | 82% |
| Alanine | .62 | 85% |
| Tryptophan | .66 | 80% |
| Methyl tryptophan | .62 | 65% |
| $NO_2$ phenyl alanine | .66 | 87% |
| Methyl tyrosine | .64 | 90% |

The amino acid methyl ester can be converted to a secondary amide by reacting the amino acid methyl ester hydrochloride with 3 equivalents of distilled ethanol amine or ethylene diamine in methanol and allowing the reaction to proceed for 2-3 days. The course of the reaction can be followed by the disappearance of the carbonyl at about 1750 $cm^{-1}$. Upon completion of the reaction, the solvent is removed under reduced pressure. The oily residue is dissolved in water and 6N HCl to pH <3, then purified on an AG 50w column, $NH_4+$. The column is washed with water until eluant is $Ag^+/H^+$ negative, and followed by a 0-2M NH4OH gradient, monitored at 254 nm. The major peak removed in 0.5-1.5M, NH40H is lyophilized. The following amino acid esters have been converted to ethanol amides (TLC in solvent 2):

| Amino Acid Ester | RF of Amide | Yield |
|---|---|---|
| Tyrosine | .74 | 89% |
| Phenyl alanine | .68 | 93% |
| Methyl tryptophan | .64 | 67% |
| $NO_2$ phenyl alanine | .65 | 94% |

The only amino acid ester treated with ethylene diamine was p-$NO_2$ phenylalanine. When the reaction was complete, the solvent was removed under reduced pressure. The oily residue is dissolved in water, and the product is extracted with tetrahydrofuran. The tetrahydrofuran solution, after back-extraction with water, yields pure product with RF 0.30 in TLC solvent 2, 60%.

Reducing Step

The reducing of the amide derivative with borane to produce a diamine is illustrated by Procedure 3 as follows:

Procedure 3 amino acid amide (1° and 2°)→R-diamine (1° and 2°)

All of the amino acid amides prepared in procedure 2 were reduced with borane in tetrahydrofuran using one equivalent of $BH_3$ for every —OH, or —NH proton, two equivalents for the carbonyl, and a surplus of one equivalent. In addition, phenylalanylglycine was reduced with nine equivalents of borane, to yield N'-Hydroxyethyl-1-benzyl ethylene diamine, as an alternative procedure.

The procedure used in reducing the amides required dissolving about 1 gm of the amide in dry tetrahydrofuran, or in combination with dry 1,2-diamethoxyethane, in a clean, oven-dried, three-neck round bottom flask fitted with a reflux condenser (capped by a $CaCl_2$ drying tube), a serum stopper, and a ground glass stopper. The assembled apparatus was flushed with dry $N_2(g)$ for 15 minutes, while the flask was cooled in an ice bath. The boranetetrahydrofuran solution (1.0M solution), was added slowly by syringe through the serum stopper at a rate of about 1.5 ml/minute. The syringe and the sides of the flask were washed with additional dry tetrahydrofuran. In some cases a while gelatinous solid appeared during the addition of the borane reagent. The serum stopper was replaced by a glass stopper, the ice bath was exchanged for a heating mantle, and the mixture was refluxed for 5 hours. The solution was cooled on ice for 20 minutes, and 50 ml of anhydrous methanol was added to the unstoppered reaction vessel. The solution that resulted was then saturated with HCl(g) and refluxed for 1 hour. The solvent was removed under reduced pressure. The primary amino acid amides reduce to vicinal diamines which solidify after removing reduction solvent. The vicinal diamines are recrystalized from either absolute ethanol or anhydrous isopropyl alcohol. The amino acid ($\beta$-hydroxyethyl)amides when reduced produce oils with removal of reduction solvent. These oils are purified by an AG 50w column ($NH_4^+$) monitored at 254 nm. The oily residue was dissolved in water and 6N HCl to pH 2, then applied to the column. The column was then eluted with water till effluent was negative to $Ag^+/H^+$, and then switched to 0–6.0M $NH_4OH$ linear gradient. The product, removed 3–5M $NH_4OH$ was then lyophilized.

Finally, when the solvent was removed from p-$NO_2$ phenylalanine ($\beta$-amino ethyl)amide reduction a solid resulted which was recrystalized from ethanol/ether. TLC in solvent 2.

The following R-diamines were prepared by the above-described Procedure 3 (wherein N′ will always herein refer to the nitrogen atom which was originally in the amide linkage):

samples prepared by classical resolution of the racemic mixture.

Reacting, or Carboxymethylating Step

Reacting of the diamine with a carboxymethylating agent is illustrated by Procedure 4, as follows.

Procedure 4

Treatment of the products of procedure 3 with carboxymethylation reagents, such as bromoacetic acid, produced chelates that vary in the number of acid groups from 3 to 5. To avoid heavy-metal-ion contamination, all $H_2O$ used was deionized and distilled into acid-washed containers, and all glassware and transfer apparatus was washed with conc. $H_2SO_4/HNO_3$ (50/50, v/v) and rinsed with $H_2O$. The ethylene diamine dihydrochloride derivative of interest was dissolved in a minimum volume of $H_2O$ in a water-jacketed reaction vessel connected to a 45° C. circulating water bath. The magnetically stirred solution was adjusted to and maintained at pH 10 with 7M KOH while 1.1 equivalents, to replace every —N—H and phenol proton, of bromoacetic acid was added in portions. By addition of KOH, the pH was kept between 10–11 for approximately 20 hours (the pH was monitored frequently during the first 3 hours). After 20 hours, the product was purified by either of the following ways.

(1) Treating of the reaction solution with conc. HCl

| Amino acid | Diamine Product | RF | Yield |
|---|---|---|---|
| Tyrosinamide | 1-(p-Hydroxybenzyl)-ethylene diamine | 0.34 | 68% |
| Phenylalaninamide | 1-benzylethylenediamine | 0.18 | 55% |
| Tryptophanamide | 1-(3-methylene indole)-ethylenediamine | 0.30 | 56% |
| Methyl tryptophanamide | 1-(1-methyl-3-methylene indole)-ethylenediamine | 0.50 | 35% |
| p-nitrophenylalaninamide | 1-(p-nitrobenzyl)ethylenediamine | 0.52 | 70% |
| Methyl tyrosinamide | 1-(p-meth oxybenzyl)ethylenediamine | 0.58 | 50% |
| Alaninamide | 1,2-propylenediamine | 0.20 | 69% |
| Phenylalanine ($\beta$-Hydroxy ethyl)amide | N′—Hydroxyethyl-1-benzyl-ethylenediamine | 0.48 | 68% |
| p-nitrophenylalanine ($\beta$-hydroxy ethyl) amide | N′—Hydroxyethyl-1-(p-nitrobenzyl)-ethylenediamine | 0.52 | 95% |
| Methyltryptophan ($\beta$-Hydroxy ethyl)amide | N′—Hydroxyethyl-1-(1-methyl-3-methylene indole) ethylenediamine | 0.44 | 30% |
| p-nitrophenylalanine ($\beta$-amino ethyl)amide | N′($\beta$-aminoethyl)-1-(p-nitrobenzyl) ethylenediamine | 0.10 | 98% |
| Phenylalanylglycine | N′—Hydroxyethyl-1-benzylethylenediamine | 0.48 | 62% |

The products of the primary amides, when reduced, form vicinal diamines which react with disodium rhodizonate. For test solutions the pH should be 5–7. All of the ethylenediamine derivatives prepared were characterized with this test. All of the products of borane reduction were characterized by the absence of carbonyl in IR scans. In addition, 1-(p-hydroxybenzyl)-ethylene diamine dihydrochloride analyzed for C,H,N,Cl gave:

Experimental: C-45.15%, H-6.53%, N-11.48%, Cl-29.35; Theory: C-45.20%, H-6.74%, N-11.72%, Cl-29.65.

The C,H,N,Cl analysis for 1-(p-nitrobenzyl)ethylenediamine dihydrochloride was:

Experimental: C-40.04%, H-5.60%, N-15.67%, Cl-26.49%; Theory: C-39.78%, H-5.87%, N-15.47%, Cl-26.19%.

As an example of the retention of optical activity, L(+)1,2-diaminopropane was $[\alpha]^{23} = +42° \pm 1$ (c 0.27, benzene). This value is 7° higher than that reported for determinations of $[\alpha]_D$ from L(+)-1,2-diaminopropane till pH was 1.8, and then evaporating solution under reduced pressure. The resulting solid was then extracted with four 5-ml portions of boiling 95% ethanol; the combined filtrates were dried under reduced pressure to an oil. The oil, dissolved in $H_2O$, was adjusted to pH 6.5, with 6N NaOH, and applied to an AG 1 anion exchange column in the formate form, 10 meq of resin per meq of product.

Or, (2) Reaction solution may be applied directly to the AG 1, formate, anion exchange column having 10 meq of resin per meq of product. The product was eluted by a linear gradient of formic acid from 1.5 to 7.0M and the column effluent was monitored at 254 nm, or in the nitro derivatives 280 nm. The major peak, which eluted between 3.5 to 5.7M formic acid was collected and lyophilized. The resultant solid was analyzed by TLC, in solvent 3 and NMR.

The following diamines were carboxymethylated (wherein, as with EDTA and ED3BA, carbon 1 of the DTPA product is and continues to be the asymmetric carbon in the alpha position of the starting amino acid):

| Starting Amine | Product | δ | RF | Yield |
| --- | --- | --- | --- | --- |
| 1-benzylethylenediamine | 1-benzyl EDTA | 2.8–4.0(13,m);7.2(5,S) | 0.90 | 62% |
| 1-(3-methylene indole)ethylenediamine | 1(3-methylene indole)EDTA | 2.2–3.4(13,m);7.0–7.5 (5,m) | 0.92 | 35% |
| 1-(p-methoxybenzyl)ethylenediamine | 1-(p-methoxybenzyl)EDTA | 2.0–3.0(13,m) 3.75(3,s) 7.0(aa$^1$bb$^1$,4,m) | 0.88 | 20% |
| N'—hydroxyethyl-1-benzylethylenediamine | N'—hydroxyethyl-1-benzyl ED3A | 2.5–3.5(15,m) 7.2(5,s) | 0.80 | 88% |
| N'—hydroxyethyl-1-(p.nitrobenzyl) ethylenediamine | N'—hydroxyethyl-1-(p-nitrobenzyl) ED3A | 2.5–3.3(15,m) 7.2(aa$^1$bb$^1$,4,m) | 0.85 | 62% |
| N'—hydroxyethyl-1-(1-methyl-3-methyleneindole)ethylenediamine | N'—hydroxyethyl-1-(1-methyl-3-methyleneindole)ED3A | 3.0–3.8(18,m) 7.0–7.7(5,m) | 0.80 | 72% |
| N'—(β-amino)ethyl-1-(p-nitrobenzyl) ethylenediamine | 1-(p-nitrobenzyl)-DTPA | 2.5–3.7(19,m) 7.5–8.0(aa$^1$bb$^1$,4,m) | 0.80 | 86% |
| Elemental analysis: $C_{21}H_{28}N_4O_{12}$ Theory: C—47.73%, H—5.30%, N—10.61% Experimental: C—47.43%, H—5.56%, N—10.37% | | | | |
| 1-(p-hydroxybenzyl)ethylenediamine | 1-(p-carboxymethoxybenzyl)EDTA | 3.0–3.7(13,m) 4.5(2,s) 6.9(aa$^1$bb$^1$,4,m) | 0.92 | 64% |
| Elemental analysis: C,H,N ($C_{19}H_{24}N_2O_{11}$) Theory: C—50.00%, H—5.26%, N—6.14% Experimental: C—50.36%, H—5.56%, N—6.31% | | | | |
| 1-(p-nitrobenzyl)ethylenediamine | 1-(p-nitrobenzyl)EDTA | 2.10–3.2(13,m) 7.5–8.2(aa$^1$bb$^1$4,m) | 0.78 | 37% |
| Elemental analysis: C,H,N,($C_{17}H_{21}N_3O_{10}$.5/2 $H_2O$) Experimental: C—43.34%, H—4.94%, N—8.93% Theory: C—43.31%, H—4.95%, N—8.91% | | | | |

Examples I–VIII further illustrate preparation of the inventive chelating agents, and Examples IX–XIII illustrate further modifications, within the scope of this invention, to increase the flexibility in uses thereof.

EXAMPLE I

L-tyrosine→L-tyrosinamide 10 g (55 mmol) L-tyrosine was treated with 300 mL methanol and 11.3 g Dowex 50Wx8 (H+) resin. The reaction mixture was stirred for three days at room temperature. After completion of the esterification, the mixture containing L-tyrosine methylester was saturated with ammonia; the resin was removed by filtration; and the filtrate was stirred for 7 days. The yield of L-tyrosinamide from L-tyrosine was 60% after recrystallization from water. The proton NMR, TLC, and mp (154°) of the product were identical to those of a sample of L-tyrosinamide from Sigma. TLC in solvent 1: $R_f$ 0.40.

EXAMPLE II

L-alanine→L-alaninamide

Starting with 10 g (112 mmol) of L-alanine, L-alaninamide was prepared by the procedure as in Example I, with a difference being that four treatments with 200 mL portions of $NH_3$-saturated methanol were required to remove 1,1 g (13 mmol) of alanine methyl ester from 22 g of Dowex resin.

EXAMPLE III

L-phenylalanine→L-p-nitro-phenylalanine amide 10.0 g (60.6 mmoles) of L-phenylalanine was dissolved in 16 ml concentrated $H_2SO_4$ (95–98%, D. 1.84 g/ml) at 0° C. 3.0 ml of $HNO_3$ (90%, D. 1.5 g/ml) was added dropwise to the stirring solution keeping temperature at about 0° C. After all of the $HNO_3$ has been added, the solution was allowed to stir 10–15 minutes. Reaction solution was then poured over about 200 ml of ice and then diluted to about 700 ml with additional $H_2O$. This solution was then heated to a boil, and neutralized with $PbCO_3$, about 80 g. The resulting precipitate was filtered and the supernatant was treated with $H_2S(g)$ to precipitate remaining Pb++, and then filtered. The resulting filtrate was reduced to ⅓ its volume. The solid which formed was filtered and washed with 95% ethanol. Yield was 50–55% of p-nitrophenylalanine when recrystallized from boiling $H_2O$.

5 g of p-nitrophenylalanine (23.8 mmoles) was dissolved with methanol saturated with HCl(g). The resulting solution was allowed to stand for 1–2 days. Solvent was removed under reduced pressure, and the resulting solid, p-nitrophenylalanine methyl ester, was recrystallized from absolute EtOH. TLC of product ester in solvent 2 showed one spot, $R_f$ 0.78 (p-nitrophenylalanine $R_f$ 0.58). Yield is 90–95% when recrystallized from absolute ethanol.

4.5 g of p-nitrophenylalanine methyl ester. HCl (17.3 mmoles) was treated with methanol saturated with $NH_3(g)$. Resulting solution was allowed to stand 3–4 days, while maintaining $NH_3$ saturation. Reaction solution was then rotoevaporated to dryness. The resulting solid, p-nitrophenylalanine amide, was recrystallized from absolute EtOH. TLC in solvent 2 shows one spot, $R_f$ 0.70 to the starting ester $R_f$ 0.78. Yield is 68–75%, m.p. 235° C. after recrystallizing from absolute ethanol.

Examples IV and VI, below, illustrate the reducing step of the provided amide derivative with borane. Example V illustrates that this reducing step preserves the original optical configuration.

EXAMPLE IV

L-tyrosinamide→L-1-(p-hydroxybenzyl)-1,2-ethylenediamine dihydrochloride

All organic solvents used in this step were dried over 3 A molecular sieves; all glassware was oven-dried and flushed with dry $N_2(g)$. 1.0 g (5.5 mmol) of L-tyrosinamide was dissolved in 220 mL of 1,2-dimethoxyethane and 50 mL tetrahydrofuran in a 3-neck round-bottom flask fitted with a reflux condenser (capped by a $CaCl_2$ drying tube), a serum stopper, and a ground glass stopper. The assembled apparatus was flushed with dry $N_2(g)$ for 15 minutes, while the flask was cooled in an ice bath. Borane-tetrahydrofuran complex, 49 mL of a 1.0M solution (49 mmol), was added slowly by syringe through the serum stopper in a 30 minute period. The syringe and the sides of the flask were washed with an additional 20 mL tetrahydrofuran. A small amount of white solid appeared during addition of the borane reagent. The serum stopper was replaced by a glass stopper, the ice bath was exchanged for a heating mantle, and the mixture was refluxed for 5 h. The solution was cooled on ice for 20 minutes, and 50 mL of anhydrous methanol was added to the unstoppered reaction vessel. The solution that resulted was then saturated with $HCl(g)$ and refluxed for 1 h. The solvent was removed under reduced pressure, and the residue was recrystallized from 95% EtOH; yield, 990 mg (68%). The product, L-1-(p-hydroxybenzyl)-1,2-ethylenediamine dihydrochloride, gave one spot by TLC in solvent 2, $R_f$ 0.34, (tyrosinamide has $R_f$ 0.74), a positive rhodizonate test for vicinal diamines, and a positive folin test for phenols. NMR (pH 6.4, $D_2O$)$\delta$=2.3–3.3 (aliphatic, 5, m), 6.8 (aromatic aa'bb', 4, m).

Anal. ($C_9H_{16}N_2OCl_2$) C, H, N, Cl— Theory: C-45.20, H-6.74, N-11.72, Cl-29.65; Experimental: C-45.15, H-6.53, N-11.48, Cl-29.35.

EXAMPLE V

L-alaninamide→L-1,2 diaminopropane

L-alaninamide was treated in a manner analogous to Example IV. Reduction of 1.1 g. (13 mmol) of L-alaninamide with 65 mmol of borane complex proceeded without formation of a precipitate. Upon addition of $HCl(g)$, the product precipitated from solution. After refluxing the mixture 1 h, 850 mg (44%) of pure 1,2 diaminopropane was collected, having $[\alpha]_D^{23}$ = +42°±1°(c 0.27, benzene), which in fact is 7° higher than that reported for determinations of $[\alpha]_D$ from L(+)-1,2-diaminopropane samples prepared by classical resolution of the racemic mixture. Accordingly, this illustrates that reduction with borane of the amide derivatives, in accordance with the present invention, does not affect the optically active center of the α-amino acid amide.

EXAMPLE VI

L-p-nitrophenylalanine amide→L-p-nitrobenzyl ethylenediamine dihydrochloride 1.50 g of p-nitrophenylalanine amide.HCl (6.2 mmoles) was dissolved in 75 ml tetrahydrofuran and cooled to 0° C. The system was closed to atmosphere and flushed with $N_2(g)$ for 20 minutes. 43.3 ml of 1.0M boranetetrahydrofuran.solution was added slowly to the stirred solution, with gases allowed to escape through a vent, over a 30–45 minute period. After the last of borane solution was added, the solution was heated to reflux for about 5 hrs, capped and vented with drying tube. After reflux, the solution was cooled in ice for about ½ hr. To the cooled solution, 50 ml MeOH is added to the opened container with stirring. The solution was then saturated with $HCl(g)$ and refluxed again for about 1 hr. Reaction solution was rotoevaporated to dryness and the resulting residue, dissolved in $H_2O$, was purified by Ag-50 W resin ($H^+$) column, with 0–7N HCl gradient. Major peak, removed in 6–7N HCl region, was lyophilized. [IR scan showed lack of C=O]. TLC in solvent 4 showed $R_f$ of product diamine 0.50 to the starting amide $R_f$ 0.78 and TLC in solvent 3 showed $R_f$ of diamine 0.50 to the amide $R_f$ 0.70. Yield was 65-70%.

Elemental Analysis: $C_9H_{15}Cl_2N_3O_2$— Theory: C-40.04%, H-5.60%, N-15.67%, Cl-26.49%; Experimental: C-39.78%, H-5.87%, N-15.43%, Cl-26.19%.

Examples VII and VIII, below, illustrate the reacting of the diamine compound with a carboxymethylating agent to yield an EDTA analog in accordance with the present invention.

EXAMPLE VII

L-1-(p-hydroxybenzyl)-1,2-ethylenediamine dihydrochloride→L-1(p-carboxymethoxy benzyl) EDTA To avoid heavy-metal-ion contamination, all $H_2O$ used was deionized and distilled into acid-washed containers, and all glassware and transfer apparatus was washed with conc. $H_2SO_4/HNO_3$ (50/50, V/V) and rinsed with $H_2O$. 734 mg (3.1 mmol) of the product from Example IV, above, was dissolved in a minimum volume of $H_2O$ (approximately 5 mL) in a water-jacketed reaction vessel connected to a 45° C. circulating water bath. The magnetically stirred solution was adjusted to and maintained at pH 10 with 7N KOH while 2.3 g (16.7 mmol) of $BrCH_2COOH$ was added in portions. By addition of KOH, the pH was kept between 10–11 for approximately 20 h (the pH was monitored frequently during the first 3 h). After 20 h, the reaction solution was adjusted to pH 1.8 with conc. HCl, and the solution was evaporated to dryness under reduced pressure. The resulting solid was extracted with four 5-mL portions of boiling 95% ethanol; the combined filtrates were dried under reduced pressure to an oil. The oil was dissolved in 5 mL $H_2O$. The solution was adjusted to pH 6.5 with 6N NaOH and applied to an AGl×4 anion exchange column in the formate form (1.5×25.5 cm resin bed). The product was eluted by a linear gradient of formic acid from 2.5 to 7.0M (total volume 1.4 L), and the column effluent was monitored at 254 nm. The major peak, which eluted between 4.1 and 5.7M formic acid, was collected and lyophilized. The resultant solid, L-1(p-carboxymethoxy benzyl)ethylenediaminetetraacetic acid, when analyzed by TLC in solvent 2, showed one spot at $R_f$ 0.16. Yield, 900 mg (64%). NMR (pH 7.5, $D_2O$)=3.0–3.7 (aliphatic, 13, m), 4.5 (ether methylene, 2, s), 6.9 (aromatic aa'bb', 4, m). $[\alpha]_D^{23}$= +25.2±0.4°(C 0.94, $H_2O$).

Anal. ($C_{19}H_{24}N_2O_{11}$) C, H, N.— Theoretical: C-50.00%, H-5.26%, N-6.14%; Experimental: C-50.36%, H-5.56%, N-6.31%.

Structure is as illustrated by Figure 5:

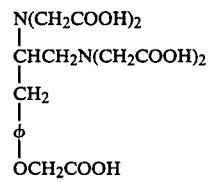

FIG. 5

EXAMPLE VIII

L-p-nitrobenzyl ethylenediamine dihydrochloride→L-p-nitrobenzyl EDTA 0.400 g of L-p-nitrobenzyl ethylenediamine.$(HCl)_2$ (1.58 mmoles), prepared as described by Example VI, above, was dissolved in H₂O/KOH to pH 10, at about 45° C.; 0.915 g of bromoacetic acid (6.63 mmoles) was added and pH was adjusted to 10-11 range with 7N KOH. Reaction was allowed to continue while stirring for 17-20 hrs, overnight. Reaction solution was then purified by AG-1 resin column (formate), with 2.0-7.0M HCOOH gradient. Product was removed in 4.8-6.2M HCOOH region. Fractions collected were combined and lyophilized. TLC in solvent 3. $R_f$ of product was 0.78, to the diamine 0.50 $R_f$. NMR in D₂O/NaOD to pH 10.0, ratio aliphatic to aromatic was 3.29 to 1, theoretical is 3.25 to 1.

Elemental analysis results: Formula: $C_{17}H_{21}N_3O_{10}.5/2H_2O$— Experimental: C-43.34%, H-4.94%, N-8.93%; Theory: C-43.31%, H-4.95%, N-8.91%.

Structure is as illustrated by Figure 6:

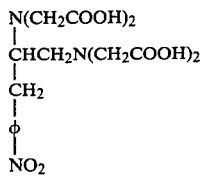

FIG. 6

EXAMPLE IX

L-p-nitrobenzyl EDTA→L-p-aminobenzyl EDTA 0.4 mmoles, 170 mg, of p-nitrobenzyl EDTA was dissolved in H₂O/NaOH to pH 11.5 and 30 mg of 10% Pd/Charcoal was added, while on ice. Reaction was allowed to stand under 1 atmosphere of H₂ for 3 hrs, in ice. A green color was observed to occur and disappear during course of the run.

After about 3 hrs the solution was filtered to remove the catalyst, then lyophilized. NMR spectrum showed expected changes in aromatic proton resonance frequencies. Also material was positive to ninhydrin. Yield: quantitative. Example IX is representative of hydrogenation of nitro derivatives of the chelating agents, to form amine derivatives thereof. Particularly, N'-hydroxyethyl-1-(p-nitrobenzyl)-EDTA has been modified by an identical hydrogenation to form the amine thereof. Such amine of N'-hydroxyethyl-1-(p-nitrobenzyl)-EDTA was further modified in a manner identical to and with results as in the description of Examples XII and XIII.

EXAMPLE X

L-p-aminobenzyl EDTA→L-p-bromoacetamidobenzyl EDTA 303.5μ mole of p-aminobenzyl EDTA was dissolved in 500 μl of H₂O and the pH of the solution was adjusted to 6.5 with 20 μl of concentrated HCl. Bromoacetyl bromide was added (46 μl) until the mixture was negative to fluorescamine. This was followed by 10 extractions with 500 μl of diethyl ether to remove excess bromoacetyl bromide. After the extractions, the pH of the solution was 1.0; it was adjusted to 2.2 by the addition of 100 μl of 1M NaOH. A white precipitate began to drop out at pH 2. The solution was placed on ice and left overnight. The mixture was then centrifuged, and the white solid washed twice with 600 μl of ice cold 0.1M HCl. The solid was dried under vacuum. Yield was 32.17 mg (61.8μ mol; 20.4%) of L-p-bromoacetamidobenzyl EDTA. TLC of the product on silica plates with solvent 3 showed only one spot with an $R_f$ of 0.96 which was both fluorescence quenching and 4-(p-nitrobenzyl)pyridine positive. Structure is as illustrated by Figure 7:

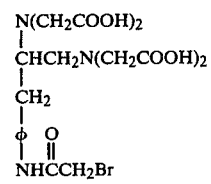

FIG. 7

EXAMPLE XI 1-(p-methoxybenzyl)-EDTA→1-(p-hydroxybenzyl)-EDTA

The chelating agent, 1-(p-methoxybenzyl) EDTA, was treated with 48% (aq) HBr/glacial acetic acid (1:5) and refluxed for 2 hours. The reaction solution was then evaporated under reduced pressure to give a white solid which was purified on AG 1, formate, column with a linear gradient of 0-7M formic acid. The major peak, removed with 2.9-3.3M formic acid, was lyophilized. The white solid that resulted was analyzed by NMR and showed lack of peak at δ3.75. Additionally, a U.V. scan at pH 3 and pH 10 showed changes in wavelength of maximum absorption from 275 nm to 295 nm, (the starting material methoxybenzyl EDTA did not exhibit any changes in U.V.). Fluorescent studies showed the material to bind $Tb^{+3}$, and $Eu^{+3}$. The products yield was 25%. The product may be further modified through phosphorylation to yield another useful chelate.

EXAMPLE XII

Acylation of L-(p-aminobenzyl) EDTA

The amino chelate derivative from Example IX, 240μ moles, was converted to the tetraethylammonium salt by eluting through an AG50w column, tetraethylammonium form, with water. The material was then lyophilized. The tetraethylammonium salt, when dried, was taken up in 1 ml of acetonitrile, dried over 3 Å sieves, and then treated with 480μ moles of any fatty acid chloride, in these cases stearoyl chloride, arachidoyl chloride, and behenoyl chloride were used, dissolved in 500 μl of dry acetonitrile or chloroform. The reaction solution was then shaken continuously for 3-5 hours, while monitoring the solution with fluorescamine. Reaction is complete when solution was fluorescamine negative. The product, which solidified during the course of the reaction, was separated by centrifuging, and drawing off the supernatant. The solid was then washed repeatedly with dry acetonitrile. The solid was then treated with H₂O and adjusted to pH 3 with 6N HCl and the solid/liquid extracted with chloroform. The solid phase was then dried. Yield was quantitative.

EXAMPLE XIII

The amino chelate derivative from Example IX, 214μ moles, was dissolved in H₂O and added to 22 μl of 85% thiophosgene in carbon tetrachloride, with stirring. Solution was monitored with fluorescamine and the reaction was complete when test was negative. The reaction solution was then evaporated under reduced pressure, leaving a white solid. This solid was then scanned on IR to detect presence of SCN- stretch at 2100 cm$^{-1}$. A TLC in solvent 3 showed solid to have Rf of 0.90 to the starting amino chelate Rf of 0.76. A sample of the solid dissolved in methanol was treated with NH$_3$(g) and an IR run after 20 minutes showed a decrease in the 2100 cm$^{-1}$ peak. Yield was quantitative.

USES AS BIFUNCTIONAL CHELATING AGENTS

The EDTA and DTPA analogs of the inventive chelating agents form stable chelates with a variety of metal ions. Such chelating is by the metal-binding portion of the molecules (that is, with the plurality of carboxylate and amine moieties thereof). Among the metal ions which may be chelated are the ionic species of the elements represented by Figure 8, below.

late rapidly air oxidized to the yellow Fe(III) chelate upon vigorous mixing. The Fe(III) chelate was protected from strong light to prevent photodecomposition. The chelate solution was analyzed for complete binding of metal ions by TLC in solvent 3; any unchelated metal ions were detected as radioactivity left at the origin. If necessary, additional chelating agent was added until TLC showed <0.5% total radioactivity left at the origin. Typically, after the chelate was formed, 350 μL of a 45 mM chelate solution (0.016 mmol) was added to 0.400 mmol of 1,2-diaminoethane dihydrochloride, and the solution was adjusted to pH 5.0 with HCl and NaHCO$_3$. Half of the solution was saved as a control. Using a freshly prepared 0.30M 1-ethyl-3-(3-dimethylaminopropyl)-carbodiimide solution, aliquots

FIG. 8

|    |    |    |    |    |    |    |    |    | 13 Al |    |    |    |    |
|----|----|----|----|----|----|----|----|----|-------|----|----|----|----|
|    | 24 Cr |    | 26 Fe | 27 Co | 28 Ni | 29 Cu |    |    | 31 Ga |    |    |    |    |
| 39 Y | 40 Zr |    | 43 Tc | 44 Ru | 45 Rh | 46 Pd |    |    | 49 In | 50 Sn |    |    |    |
| 57 La | 72 Hf |    |    | 76 Os | 77 Ir |    |    | 80 Hg |    |    | 83 Bi |    |    |
| 89 Ac |    |    |    |    |    |    |    |    |    |    |    |    |    |

| 58 | 59 | 60 | 61 | 62 | 63 | 64 | 65 | 66 | 67 | 68 | 69 | 70 | 71 |
|----|----|----|----|----|----|----|----|----|----|----|----|----|----|
| Ce | Pr | Nd | Pm | Sm | Eu | Gd | Tb | Dy | Ho | Er | Tm | Yb | Lu |
| 90 | 91 | 92 | 93 | 94 | 95 | 96 | 97 | 98 | 99 | 100 | 101 | 102 | 103 |
| Th | Pa | U | Np | Pu | Am | Cm | Bk | Cf | Es | Fm | Md | No | Lw |

When it is desired that the EDTA analogs be used as binfunctional chelating agents—that is, that the EDTA analogs include a covalent bond-forming moiety for attachment of the EDTA analogs to biological molecules and the like—the EDTA analogs may be, if necessary, easily modified to include such a covalent bond-forming moiety. As may be understood, the term "covalent bond-forming moiety" includes, for example, amino and carboxyl groups which are easily attached by carbodiimide coupling to form peptide bonds with biological molecules.

Thus, for example, the EDTA analog represented by FIG. 6 of Example VIII may be readily converted from having the para-substituted nitro group to a para-substituted amino group by reaction under 1 atmosphere of hydrogen with a catalyst such as 10% Palladium/charcoal. As illustrated by Example X, the amino group of this EDTA analog may be easily further modified so as to provide that the covalent-bond forming moiety functions as an alkylating moiety for the EDTA analog.

The EDTA analog represented by Figure 5 of Example VII already has a para-substituted carboxyl group available for coupling to a biological molecule, and thus would not usually be further modified. Example XIV, below, illustrates the coupling of this EDTA analog in the Fe(III) chelate form to human serum albumin.

EXAMPLE XIV

A. Coupling Of An EDTA Analog To Ethylenediamine

Formation of an Fe(III) chelate with L-1(p-carboxymethoxy benzyl)-EDTA effectively protects, or blocks, the EDTA carboxyl groups of the metal binding portion from the carbodiimide coupling reaction at the covalent binding portion.

With a trace amount of radioactive $^{59}$FeCl$_3$, the Fe(III) chelate was made by adding FeSO$_4$ to the compound as in FIG. 5 at pH 2.0; the colorless Fe(II) checontaining ⅛ mole of carbodiimide per mole chelate were then added to the reaction solution. One hour after each addition, high voltage paper electrophoresis analysis was performed in a 1.11 m acetic acid solution. The reaction and control solutions were applied to the center of the paper. Each electrophoresis was run at 4000 v for 30 min. The paper was then dried and the position of colored iron chelates noted. The paper was treated with ninhydrin, and 2 cm sections were cut and counted. The desired coupling product was located at the origin as determined by radioactivity, a positive ninhydrin test, and by the yellow color of the Fe(III) chelate.

B. Coupling Of the EDTA Analog Chelate To Human Serum Albumin

Normal human serum albumin, 25% in saline solution, was dialyzed at 4° C. for four days against 3 changes of 0.9% NaCl. The Fe(III) chelate from subpart A, above, had a tracer amount of $^{59}$FeCl$_3$ added. Typically, 640 μL of the 0.22M Fe(III) chelate solution (141μ mol) at pH 5.0 was added to 240 μL of a 2.7 mM albumin solution (0.65μ mol) at the same pH in 0.9% NaCl. A total of 28 μL of a freshly prepared 0.18M carbodiimide solution (5.0 mol) was added to the reaction solution at room temperature in order to obtain approximately 0.5 chelate covalently bound per albumin molecule. Polyacrylamide gel electrophoresis indicated no cross-linking of albumin during the coupling reaction. Initial analysis of the product involved Bio-Gel P-100 gel filtration of an aliquot of the reaction mixture in a 0.7×9 cm column eluted with 0.9% NaCl, and $^{59}$Fe counting of the fractions (0.5±0.1 chelate per albumin). A nonspecific binding control was also performed. Of the radioactivity shown by gel filtration to be bound to protein, 95% was removed by dialysis of the reaction mixture overnight at 4° C. and pH 5.0 against 2 changes of 50 mM EDTA, 50 mM citrate, and 34 mM ascorbate. The labeled protein was dialyzed at 4° C. against 0.1M citrate, pH 5.0, for 8 days. A fluorescence titration using terbium(III) yielded a value of 0.5±0.05 chelate per albumin. Addition of radiolabelled indium(III) in excess to an aliquot of protein, and subsequent analysis by Bio-Gel P-100 column chromatography yielded a value of 0.5±0.05 chelate per albumin, in excellent agreement with the other measurements. A control of normal albumin (dialyzed in exactly the same manner) did not show any significant indium binding.

In the case of the Fe(III) chelate of the EDTA analog coupled to human serum albumin, described by subpart B of Example XIV, above, iron may be easily removed after reduction to Fe(II) by dialysis against a buffer containing ascorbate, EDTA, and citrate at pH 5. The iron-free protein-chelate conjugate may then be labelled rapidly with a short-lived, radionuclide such as $^{111}$indium, and the radiolabelled protein used as a radiopharmaceutical.

The use of terbium or europium chelates of EDTA analogs formed from L-tyrosinamide and L-p-nitrophenylalaninamide (such as the analogs of Figures 5 and 6) in fluorescence energy transfer studies is particualrly attractive because the aromatic rings thereof lead to enhanced luminescence intensity from the chelated lanthanides. Also, the use of an EDTA analog formed from an L-cysteine amide is attractive for coupling with certain biological molecules via disulfide bonds, rather than the peptide bond formation previously described.

In summary, the present invention discloses that the amide derivatives of α-amino acids can be easily converted into EDTA, ED3A or DTPA analogs with retention of configuration at the asymmetric carbon thereof. Such EDTA, ED3A and DTPA analogs are particularly useful as bifunctional chelating agents wherein a covalent bond forming moiety of the EDTA analog, ED3A analog, or of the DTPA analog may be attached to a biological molecule in such a way that the product retains biological activity, and can serve as an in vivo radiotracer when the metal binding moiety of the EDTA, ED3A or DTPA analog has formed a chelate with an appropriate radioactive metal ion.

We claim:

1. An optically active and substantially optically pure chelating agent comprising:
   an EDTA, ED3A, or DTPA analog having a central ethylene moiety, said ethylene moiety being substituted at a one carbon thereof by an R moiety substituent, said R moiety substituent being an amino acid side group including a methylene group through which said amino acid side group is bonded, and selected from the group consisting of $-CH_2-\phi$, $-CH_2-SH$, $-CH_3$, $-(CH_2)_4-NH_3^+$, $-CH_2-\phi-OH$, $-CH_2-\phi-OCH_3$,

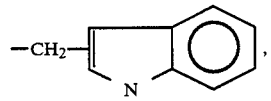

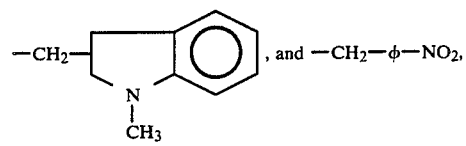, and $-CH_2-\phi-NO_2$, said one carbon defining an L or D stereochemical configuration for said EDTA, ED3A or said DTPA analog.

2. A chelating agent having the structure $$\begin{array}{c} R_1 \\ | \\ R-CH-CH_2-NCH_2COOH \\ | \\ N \\ (CH_2COOH)_2 \end{array}$$

wherein $R = -CH_2-\phi$, $-CH_2-\phi-OCH_2COOH$, $-CH_2-\phi-NO_2$ $-CH_2-\phi-NH_2$, $-CH_2-\phi-NH\overset{O}{\overset{\|}{C}}CH_2Br$, $-CH_2-\phi-OCH_3$ $-CH_2\phi OH$, 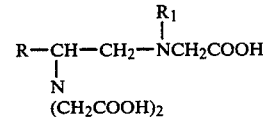,

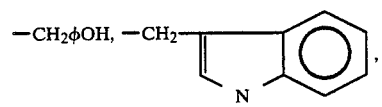

$-CH_2-\phi-NCS$, $-CH_2-\phi-N_2^+$, $-CH_2-\phi N_3$  $-CH_2-\phi-\overset{O}{\overset{H\|}{NC}}-(CH_2)_{16}CH_3$, $-CH_2-\phi-\overset{O}{\overset{H\|}{NC}}-(CH_2)_{18}CH_3$ or $-CH_2-\phi-\overset{H}{N}-\overset{O}{\overset{\|}{C}}-(CH_2)_{20}CH_3$ and $R_1 = -CH_2COOH$, $-CH_2CH_2OH$, or $-CH_2-CH_2N(CH_2COOH)_2$ 3. An optically active and substantially optically pure chelating agent having the structure $$\begin{array}{c} R_1 \\ | \\ R-CH-CH_2-NCH_2COOH \\ | \\ N(CH_2COOH)_2 \end{array}$$

wherein $R_1$ is $-CH_2COOH$, $-CH_2CH_2OH$, or $-CH_2CH_2N(CH_2COOH)_2$ and R is an alpha amino acid side group selected from the group consisting of leucine, phenylalanine, tryptophan, methionine, serine, cysteine, tyrosine, methyl tyrosine, methyl tryptophan, and p-nitrophenylalanine.

4. An optically active and substantially optically pure chelating agent having the structure

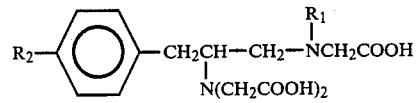

wherein $R_1$ is $-CH_2CO_2H$, $CH_2CH_2OH$, or $-CH_2CH_2N(CH_2COOH)_2$, and $R_2$ is selected from the group consisting of $-OH$, $NH_2$, and $-NO_2$.

* * * * *

UNITED STATES PATENT AND TRADEMARK OFFICE
CERTIFICATE OF CORRECTION

PATENT NO. : 4,622,420

DATED : November 11, 1986

INVENTOR(S) : Claude F. Meares, et al.

It is certified that error appears in the above-identified patent and that said Letters Patent is hereby corrected as shown below:

The following paragraph should appear in Column 1, line 3, immediately following the title:

This invention was made with Government support under contract CA28343 awarded by the National Institute of Health. The Government has certain rights in this invention.

Signed and Sealed this

Eleventh Day of April, 1995

Attest:

BRUCE LEHMAN

*Attesting Officer*     *Commissioner of Patents and Trademarks*